United States Patent [19]

Poss

[11] Patent Number: 5,177,097

[45] Date of Patent: Jan. 5, 1993

[54] ACYL AMIDINE AND ACYL, GUANIDINE SUBSTITUTED BIPHENYL DERIVATIVES

[75] Inventor: Michael A. Poss, Lawrenceville, N.J.

[73] Assignee: E. R. Squibb & Sons, Inc., Princeton, N.J.

[21] Appl. No.: 735,398

[22] Filed: Jul. 24, 1991

[51] Int. Cl.⁵ .................. A61K 31/415; C07D 233/88; C07D 233/70
[52] U.S. Cl. .................... 514/386; 514/389; 548/323.5; 548/316.4; 548/321.5; 548/314.4; 548/324.1; 548/312.1; 548/312.7; 548/314.7; 548/112; 548/319.1; 548/319.5; 548/320.5; 548/317.1
[58] Field of Search ............... 548/301, 308; 514/386, 514/389

[56] References Cited

U.S. PATENT DOCUMENTS

| | | | |
|---|---|---|---|
| 4,340,598 | 7/1982 | Furukawa et al. | 424/273 |
| 4,355,040 | 10/1982 | Furukawa et al. | 424/273 |
| 4,582,847 | 4/1986 | Furukawa et al. | 514/400 |
| 4,812,462 | 3/1989 | Blankley et al. | 514/303 |
| 4,816,463 | 3/1989 | Blankley et al. | 514/293 |
| 4,820,843 | 4/1989 | Aldrich et al. | 548/252 |
| 4,870,186 | 9/1989 | Aldrich et al. | 548/215 |
| 4,874,867 | 10/1989 | Aldrich et al. | 548/101 |
| 4,880,804 | 11/1989 | Carini et al. | 514/234 |

FOREIGN PATENT DOCUMENTS 253310  9/1987  European Pat. Off. .
323841  5/1989  European Pat. Off. .
324377  5/1989  European Pat. Off. .

Primary Examiner—Mary C. Lee
Assistant Examiner—Mary Susan H. Gabilan
Attorney, Agent, or Firm—Ellen K. Park

[57] ABSTRACT

Novel compounds are disclosed having the formula

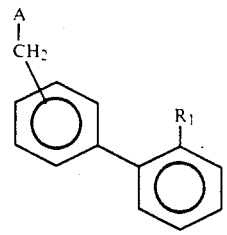

where A is

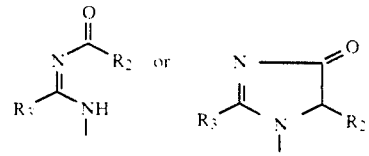

and wherein $R_1$, $R_2$ and $R_3$ are as defined herein. These compounds inhibit the action of angiotensin II and are useful, therefore, for example, as antihypertensive agents.

8 Claims, No Drawings

ACYL AMIDINE AND ACYL, GUANIDINE SUBSTITUTED BIPHENYL DERIVATIVES

FIELD OF THE INVENTION

The present invention relates to novel substituted acyl amidines and acyl guanidines which are useful as antihypertensive agents.

SUMMARY OF THE INVENTION

In accordance with the present invention, novel compounds which inhibit the action of the hormone angiotensin II are disclosed. These compounds are of the general formula

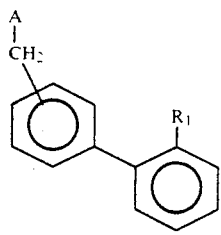

where A is

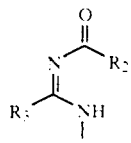

or

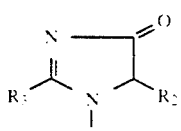

and pharmaceutically acceptable salts thereof; where $R_1$ is hydrogen, —COOH, —NHSO$_2$CF$_3$,

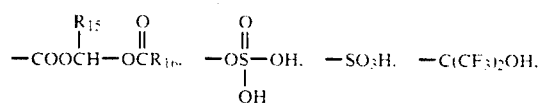

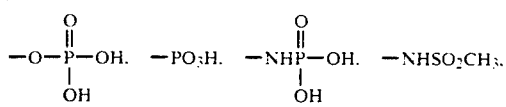

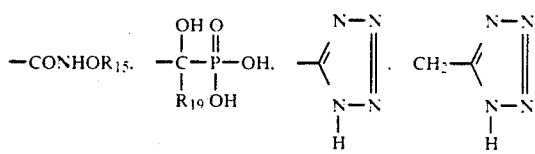

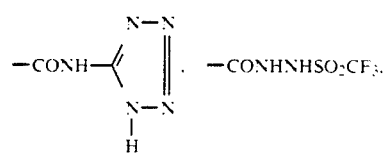

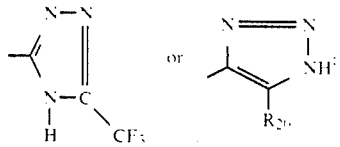

$R_2$ is H, alkyl of 1 to 10 carbon atoms, alkenyl of 3 to 10 carbon atoms, or the same groups substituted with F; phenylalkenyl wherein the aliphatic portion is 2 to 6 carbon atoms; —(CH$_2$)$_m$-imidazol-1-yl; —(CH$_2$)$_m$-1,2,3-triazolyl optionally substituted with one or two groups selected from CO$_2$R$_2$ or alkyl of 1 to 4 carbon atoms; —(CH$_2$)$_m$-tetrazolyl; —(CH$_2$)$_n$OR$_6$;

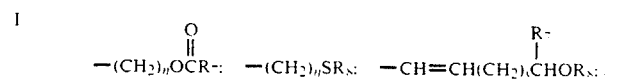

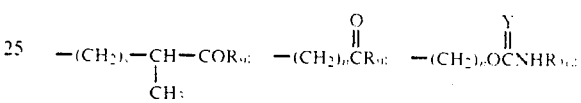

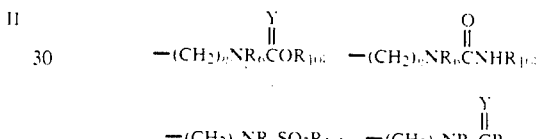

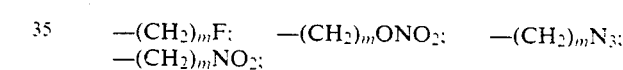

—(CH$_2$)$_m$F; —(CH$_2$)$_m$ONO$_2$; —(CH$_2$)$_m$N$_3$; —(CH$_2$)$_m$NO$_2$;

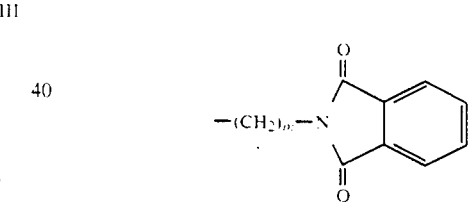

$R_2$ is alkyl of 2 to 10 carbon atoms, alkenyl or alkynyl of 3 to 10 carbon atoms or the same groups substituted with F or CO$_2$R$_7$; cycloalkyl of 3 to 8 carbon atoms, cycloalkylalkyl of 4 to 10 carbon atoms; cycloalkylalkenyl or cycloalkylalkynyl of 5 to 10 carbon atoms; —(CH$_2$)$_s$Z(CH$_2$)$_m$R' (wherein R' is H, C$_{1-6}$alkyl, C$_{3-6}$-cycloalkyl, C$_{2-4}$alkenyl or C$_{2-4}$alkynyl) optionally substituted with F or CO$_2$R$_7$; benzyl or benzyl substituted on the phenyl ring with 1 or 2 halogens, alkoxy of 1 to 4 carbon atoms, alkyl of 1 to 4 carbon atoms or nitro;

$R_6$ is H, alkyl of 1 to 6 carbon atoms, cycloalkyl of 3 to 6 carbon atoms, phenyl or benzyl;

$R_7$ is H, alkyl or perfluoroalkyl of 1 to 8 carbon atoms, cycloalkyl of 3 to 6 carbon atoms, phenyl or benzyl;

$R_8$ is H, alkyl of 1 to 6 carbon atoms, cycloalkyl of 3 to 6 carbon atoms, phenyl, benzyl, acyl of 1 to 4 carbon atoms, phenacyl;

$R_9$ is H, alkyl of 1 to 6 carbon atoms, cycloalkyl of 3 to 6 carbon atoms, (CH$_2$)$_p$C$_6$H$_6$, OR$_{11}$ or NR$_{12}$R$_{13}$;

$R_{10}$ is alkyl of 1 to 6 carbon atoms or perfluoroalkyl of 1 to 6 carbon atoms, 1-adamantyl, 1-naphthyl, 1-(1-naphthyl)ethyl, or (CH$_2$)$_p$C$_6$H$_5$;

$R_{11}$ is H, alkyl of 1 to 6 carbon atoms, cycloalkyl of 3 to 6 carbon atoms, phenyl or benzyl;

$R_{12}$ and $R_{13}$ independently are H, alkyl of 1 to 4 carbon atoms, phenyl, benzyl, α-methylbenzyl, or taken together form a ring of the formula

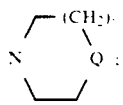

Q is $NR_{14}$, O or $CH_2$;

$R_{14}$ and $R_{15}$ are independently H, alkyl aryl, aralkyl or cycloalkyl;

$R_{16}$ is $C_{1-6}$alkyl, $-NR_{17}R_{18}$ or

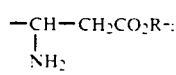

$R_{17}$ and $R_{18a}$ are independently H, $C_{1-6}$-alkyl, benzyl or taken together are 3 to 6 carbon atoms forming a 4- to 7-membered ring with the nitrogen atom to which they are attached;

$R_{19}$ is H, $C_{1-5}$alkyl, phenyl;

$R_{20}$ is $-CN$, $-NO_2$ or $-CO_2R_7$;

X is a halogen preferably bromine;

Y = O or S;

Z = O, $NR_6$ or S;

m is 1–5;

n is 1–10;

p is 0–3;

s is 0–5;

t is 0 or 1.

DETAILED DESCRIPTION OF THE INVENTION

The present invention relates to the compounds of formula I and to pharmaceutical compositions and methods employing such compounds.

The term "aryl", as used throughout the specification either by itself or as part of a larger group, refers to phenyl or phenyl substituted with one or more groups selected from halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

The term "alkyl", as used throughout the specification either by itself or as part of a larger group, refers to groups having 1 to 10 carbon atoms. Alkyl groups having 1 to 4 carbon atoms are preferred.

The term "cycloalkyl", as used throughout the specification either by itself or as part of a larger group, refers to groups having 3 to 7 carbon atoms.

The term "alkoxy", as used throughout the specification either by itself or as part of a larger group, refers to groups having 1 to 8 carbon atoms. Alkoxy groups having 1 to 3 carbon atoms are preferred.

The term "halogen", as used by itself or as part of a larger group refers to fluorine, chlorine, bromine and iodine with bromine being preferred.

To prepare the compounds of formula I where A is the moiety represented by the formula II, a compound of formula

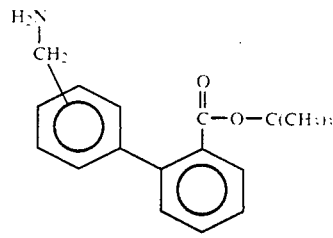

is combined with a compound of formula

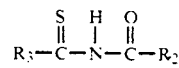

in a solvent such as dimethylformamide in the presence of a base such as triethylamine and a coupling agent such as ethyl-3-(3-dimethylamino)propyl-carbodiimide-hydrochloride to form compounds of formula

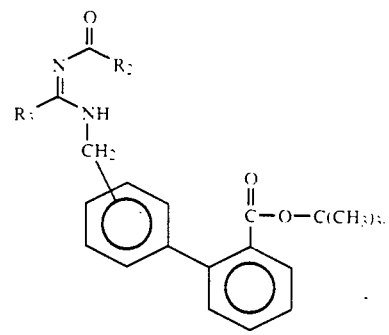

Compounds of formula VI are then treated with a strong acid such as hydrochloric acid in an organic solvent such as dioxane to form compounds of formula

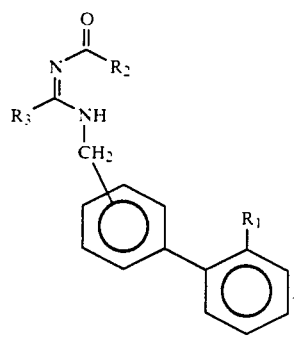

Compounds of formula IV may be prepared by reacting a compound of formula

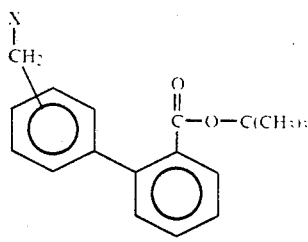 VII where X is bromine with sodium azide in a solvent such as dimethylformamide to form the azide

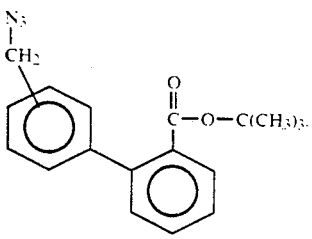 VIII

The azide VIII is then reacted with hydrogen in the presence of a catalyst such as palladium on carbon in a solvent such as methanol to form the amine of formula IV.

Compounds of formula VII can be prepared by methods disclosed in European Patent Application 0 253 310, published Jan. 20, 1988.

Compounds of formula V may be prepared by reacting a thioamide or thiourea with an anhydride or acyl chloride in the presence of a base such as sodium hydride in a solvent such as tetrahydrofuran.

To prepare compounds of formula I where A is the moiety represented by formula III, a compound of formula VII is combined with a base such as sodium bicarbonate in a solvent such as dimethylsulfoxide to form an aldehyde of formula

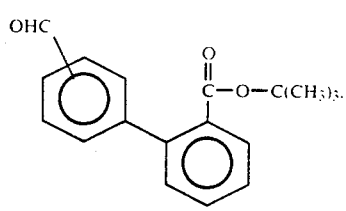 IX

The aldehyde of formula IX is then mixed with an ester of the formula $$NH_2-CH(R_2)-CO_2CH_2CH_3 \quad X$$

such as DL-alanine ethyl ester-hydrochloride in a solvent such as methanol and treated with a reducing agent such as sodium cyano borohydride to form a compound of formula

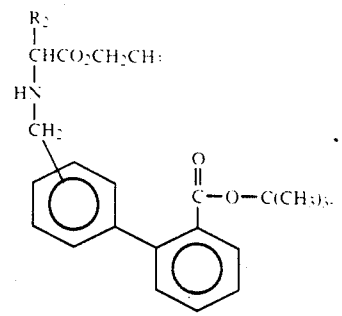 XI

The compound of formula XI is then combined with a compound of formula

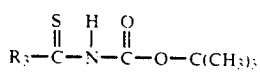 Va to form a compound of formula

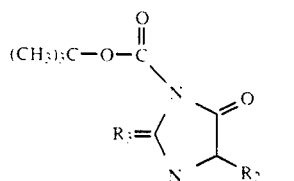 XII

Compounds of formula XII are then treated with a strong acid such as hydrochloric acid in an organic solvent such as dioxane to form compounds of formula

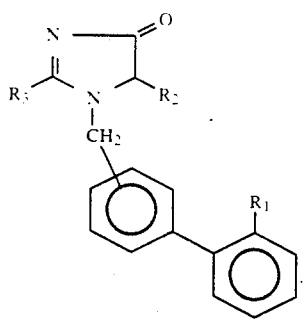 Ib

Preferred compounds of the present invention are those wherein
$R_1$ is COOH, tetrazole;
$R_2$ is methyl, ethyl, $-CH_2OH$; and
$R_3$ is n-butyl, n-propyl, NH-n-propyl, and the substitution is at the para position Most preferred are compounds of formula Ia wherein
$R_1$ is COOH, tetrazole;
$R_2$ is methyl; and $R_3$ is propylamino or n-butyl; and compounds of formula Ib wherein
$R_1$ is COOH;
$R_2$ is methyl;
$R_3$ is propylamino; and the substitutions are at the para position The present compounds of formula I inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention inhibit the action of A-II at its receptors on target cells and thus prevent the increase in blood pressure produced by this hormone-receptor interaction. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but intranasal, transdermal and parenteral routes such as the subcutaneous, intramuscular, intravenous or intraperitoneal routes can also be employed. Further the compounds of this invention are believed to be useful in the treatment of congestive heart failure and cardiac hypertrophy.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

4.-[[[[(Methoxycarbonyl)imino](propylamino)methyl]amino]methyl][1,1'-biphenyl]-2-carboxylic acid, monopotassium salt

A. Propylthiourea

Benzoyl isothiocyanate (3.37 mL, 25.0 mmol, 1.0 eq) was dissolved in chloroform (50 mL, 0.5 M) and treated dropwise with propylamine (2.26 mL, 27.5 mmol, 1.1 eq). The mixture was stirred at room temperature one hour and then taken to dryness in vacuo to give a yellow solid. The solid was partially dissolved in methanol (61 mL) and water (26 mL) and potassium carbonate (6.91 g, 2.0 eq) was added. The mixture was heated under reflux 2.5 hours. The methanol was removed in vacuo and the residue was partitioned between 1 N sodium hydroxide solution and 10% methanol in chloroform. The layers were separated and the aqueous was reextracted with 10% methanol in chloroform (2×50 mL). The combined organic layers were dried (magnesium sulfate), filtered and freed of solvent in vacuo leaving a yellow solid. This was triturated with ether and dried in vacuo to give the title compound (1.59 g, 54%), m.p. 103°-107° C.

B. [(Propylamino)thioxomethyl]carbamic acid, methyl ester

The title A compound (331 mg, 2.8 mmol, 1.0 eq.) was dissolved in distilled tetrahydrofuran (14 mL, 0.2 M), cooled to 0° C. and treated with sodium hydride (336 mg of 50% in mineral oil, 7 mmol, 2.5 eq.). The mixture was stirred cold 30 minutes and methyl chloroformate (269 µl, 3.5 mmol, 1.25 eq) was added. After stirring at 0° C. for 2.5 hours, the reaction was quenched by adding saturated aqueous ammonium chloride solution. The product was extracted into chloroform dried (magnesium sulfate), freed of solvent in vacuo and purified by chromatography on silica gel (50 g) eluting with ether:hexane (1:5) to give the title compound (174 mg, 35%) as a white solid. TLC:$R_f$=0.36, silica gel, ether:hexane (1:2), UV.

C. 4'-Methyl[1,1'-biphenyl]-2-carboxylic acid, 1,1-dimethylethyl ester

[Reference: European Patent Application 87-109919.8 example 85a, page 148 line 22]To a solution of 4'-methyl[1,1'-biphenyl]-2-carboxylic acid (25.0 g, 0.118 mol) in dichloromethane (120 mL) at 0° C. was added oxalyl chloride (2.0 M solution in methylene chloride (470 mL, 0.236 mol) over 30 minutes. The solution was warmed to 25° C., stirred for three hours and concentrated in vacuo to remove excess oxalyl chloride. The remaining residue was suspended in diethyl ether (300 mL), cooled to 0° C. and potassium t-butoxide (26.44 g, 0.236 mol) was added over 15 minutes keeping the temperature of the mixture between 15°-25° C. The mixture was allowed to warm to 25° C. and was stirred for one hour, poured into water (200 mL), and extracted with diethyl ether. The ether extract was then washed with aqueous sodium bicarbonate (saturated solution), dried (magnesium sulfate) and concentrated in vacuo to an amber oil. Subsequent distillation (124°-130° C., 0.6 mm Hg) yielded the title compound as a colorless liquid (27.7 g, 92%).

D. 4'-(Bromomethyl)[1,1'-biphenyl]-2-carboxylic acid, 1,1-dimethylethyl ester.

A mixture of the title C compound (13.42 g, 50.0 mmol), N-bromosuccinimide (8.9 g, 50 mmole) and azobisisobutylronitrile (10 mg) was refluxed under argon in carbon tetrachloride (50 mL) for two hours. The mixture was cooled to 25° C. and concentrated in vacuo. The residue was stirred in dichloromethane (200 mL), and filtered to remove insoluble material. The filtrate was then filtered through silica gel (200 g held in a fritted buchner funnel), washed with dichloromethane (200 mL), and concentrated to dryness in vacuo. Recrystallization of the solid residue from petroleum ether (16.55 g in 800 mL) produced the title compound, as a white crystalline solid (14.0 g, 72% yield), mp 98°–101° C.

E. 4'-(Azidomethyl)[1,1'-biphenyl]-2-carboxylic acid, 1,1-dimethylethyl ester The title compound D (6.007 g, 17.3 mmol, 1.0 eq) was dissolved in dimethylformamide (86 mL, 0.2 M). Sodium azide (2.81 g, 43.25 mmol, 2.5 eq) was added and the mixture was left stirring overnight at room temperature. Water (400 mL) was added and the product was extracted into ether:hexane (1:1). The combined organic extracts were washed twice with water and once with saturated sodium chloride solution, dried (magnesium sulfate) and freed of solvent in vacuo leaving the title compound (5.36 g, quantitative). TLC, silica gel, $R_f=0.36$, 10% ether in hexane, UV.

F. 4'-(Aminomethyl)[1,1'-biphenyl]-2-carboxylic acid, 1,1-dimethylethyl ester The title E compound (17.3 mmol, 1.0 eq) was dissolved in methanol (60 mL), treated with 5% palladium on carbon (300 mg) and hydrogenated on a Parr shaker at up to 50 psi for 18 hours. The catalyst was removed by filtration and the solvent was removed in vacuo. The remaining material was chromatographed on silica gel (200 g). A fast-moving impurity was eluted with 3% methanol in dichloromethane containing 0.2% ammonium hydroxide. The desired amine was then eluted with 5% methanol in dichloromethane containing 0.2% ammonium hydroxide followed by 8% methanol in the same mixture to give the title compound (3.94 g, 80%) as a viscous oil.

TLC:silica gel, $R_f=0.39$, 10% methanol in methylene chloride+ammonium hydroxide, UV.

G. 4'-[[[[(Methoxycarbonyl)imino](propylamino)methyl]amino]methyl][1,1'-biphenyl]-2-carboxylic acid, 1,1-dimethylethyl ester.

The title B compound (102 mg, 0.579 mmol, 1.0 eq) was dissolved in dimethylformamide (0.7 mL), cooled to 0° C. and treated with a solution of the title F compound (164 mg, 0.579 mmol, 1 eq) in DMF (0.5 mL, final conc. 0.5 M). Triethylamine (122 μl, 0.87 mmol, 1.5 eq) and ethyl-3-(3-dimethylamino) propyl carbodiimide.hydrochloride (133 mg, 0.69 mmol, 1.2 eq) were added. The mixture was stirred cold one hour, at room temperature overnight, then at 40° C. for four hours. Water was added and the product was extracted into ether (3×15 mL). The combined ether extracts were washed with saturated sodium bicarbonate solution and saturated sodium chloride solution, dried (magnesium sulfate) and freed of solvent in vacuo. The remaining material was chromatographed on silica gel (20 g), eluting with 10% acetone in hexane followed by 20% acetone in hexane to give the title compound (194 mg, 79%). TLC:$R_f=0.38$, silica gel, 30% acetone in hexane, UV and Rydon.

H. 4'-[[[[(Methoxycarbonyl)imino](propylamino) methyl]amino]methyl][1,1'-biphenyl]-2-carboxylic acid, monopotassium salt.

The title G compound (168 mg, 0.39 mmol, 1.0 eq) was cooled in an ice bath and treated with cold 4 N hydrochloric acid in dioxane (9.0 mL, 9 eq). The mixture was stirred cold one hour and then at room temperature 3.5 hours. The solvent was removed in vacuo. The residue was dissolved in a small amount of water and 1N potassium hydroxide was added until the pH reached 9. The aqueous solution was applied to an HP-20 column (20 mL). The column was eluted with water until the eluate was no longer strongly basic and the product was then eluted with increasing percentages of acetone in water (1, 3, 5, 10%). The fractions containing the desired material were concentrated to a small volume in vacuo and lyophilized. The product was redissolved in water, passed through a polycarbonate membrane and relyophilized to give the title compound (139 mg, 84%).

EXAMPLE 2

4'-[[[1-[(Methyoxycarbonyl)imino]pentyl]amino]methyl][1,1'-biphenyl]-2-carboxylic acid, monopotassium salt.

A. Pentanamide

Valeric acid (10.86 mL, 100 mmol, 1.0 eq) was dissolved in chloroform (100 mL, 0.1 M) and cooled to −20° C. Ethyl chloroformate (9.52 mL, 100 mmol, 1 eq) was added. Triethylamine (14.0 mL, 100 mmol, 1.0 eq) was then added dropwise over 5 minutes. The mixture was stirred at −20° C. for 30 minutes. Ammonia was bubbled through the mixture 10 minutes at −20° C. and 20 minutes at 0° C. The mixture was then allowed to warm to room temperature and stirred for 90 minutes. Chloroform (100 mL) and 1 N hydrochloric acid (50 mL) were added. The layers were separated and the organic layer was washed with saturated sodium bicarbonate solution, dried (magnesium sulfate), filtered and freed of solvent in vacuo. Trituration with isopropyl ether gave the title compound (6.315 g, 62%) as a white solid.

B. Pentanethioamide

The title A compound (5.0 g, 49.4 mmol) was dissolved in distilled tetrahydrofuran (100 mL, 0.5 M) and treated with Lawesson's Reagent (11.97 g, 29.6 mmol, 0.6 eq). The mixture was stirred at room temperature 4.5 hours, then freed of solvent in vacuo. The residue was chromatographed on silica gel (200 g) eluting with ether:hexane mixtures (2:3 followed by 1:1 followed by 2:1) to give the title compound (3.53 g, 61%) as a white solid.

TLC:$R_f=0.4$, silica gel, diethyl ether:hexane (2:1), UV and Cerium.

C. [1-Thioxopentyl]carbamic acid, methyl ester

The title B compound (328 mg, 2.8 mmol, 1.0 eq) was dissolved in distilled tetrahydrofuran (14 mL, 0.2M) and cooled to 0° C. Sodium hydride 50% in mineral oil, 336 mg, 7 mmol, 2.5 eq) was added and the mixture was stirred cold 30 minutes. Methyl chloroformate (269 μl, 3.5 mmol, 1.25 eq) was added and the mixture was stirred cold for one hour. The reaction was then quenched with saturated ammonium chloride solution and the product was extracted into chloroform, dried (magnesium sulfate), and freed of solvent in vacuo. The remaining material was chromatographed on silica gel (50 g) eluting with ether:hexane (1:5) to give the title compound (152 mg, 31%) TLC:$R_f$=0.55, silica gel, ether:hexane (1:2), UV and Cerium.

D.
4'-[[[1-[(Methoxycarbonyl)imino]pentyl]amino]methyl][1,1'-biphenyl]-2-carboxylic acid, 1,1-diphenylmethyl ester The title C compound (92 mg, 0.525 mmol, 1.0 eq) was dissolved in dimethylformamide (0.55 mL, 1 M) and the solution was cooled in an ice bath. A solution of the title D compound of Example 1 (148.5 mg, 0.525 mmol, 1.0 eq) in dimethylformamide (0.5 mL) was added (final concentration 0.5 M). Triethylamine (103 μl, 0.78 mmol, 1.5 eq) and ethyl-3-(3-dimethylamino) propyl carbodiimide.hydrochloride acid (120 mg, 0.63 mmol, 1.2 eq) were added. The mixture was stirred cold 1 hour and at room temperature 2.5 hours. Water (10 mL) was then added. The product was extracted into ether (3×15 mL). The combined extracts were washed once with saturated sodium bicarbonate solution and once with saturated sodium chloride solution, dried (magnesium sulfate) and freed of solvent in vacuo. The remaining yellow oil was purified by chromatography on silica gel (20 g) eluting with 10% acetone in hexane to give the title compound (188 mg, 84%). TLC:$R_f$=0.35 silica gel, 30% acetone in hexane, UV and Rydon spray.

E.
4'-[[[1-[(Methoxycarbonyl)imino]pentyl]amino]methyl][1,1'-biphenyl]-2-carboxylic acid, monopotassium salt.

The title D compound (165 mg, 0.388 mmol) was cooled in an ice bath and treated with a 4 N solution of hydrochloric acid in dioxane (9 mL, ~9.5 eq). The mixture was stirred cold one hour and at room temperature 5 hours, then taken to dryness in vacuo. The residue was dissolved in water and treated with 1 N potassium hydroxide until the solution was strongly basic. The solution was applied to a column of HP20 (25 mL), eluting the inorganics with water and then eluting the desired potassium salt with 5% acetone in water followed by 10% acetone in water. The fractions containing the product were combined, concentrated to a small volume and lyophilized. This product was then redissolved in water, passed through a polycarbonate membrane and relyophilized to give the title compound (128 mg, 79%).

EXAMPLE 3

4'-[[4,5-Dihydro-5-methyl-4-oxo-2-(propylamino)-1H-imidazol-1-yl]methyl]-[1,1'-biphenyl]-2-carboxylic acid, trifluoroacetate (1:1) salt

A. 4'-Formyl[1,1'-biphenyl]-2-carboxylic acid, 1,1-dimethylethyl ester

The title D compound from Example 1 (1.2739 g, 3.67 mmol, 1.0 eq) and sodium bicarbonate (616.4 mg, 7.337 mmol, 2.0 eq) were combined in dimethylsulfoxide (3.7 mL, 1M) and heated at 120° C. for 15 minutes. The mixture was cooled to room temperature, water (20 mL) was added and the product was extracted into ether:hexane (3:2, 3×20 mL). The combined extracts were washed with water (2×15 mL), dried (sodium sulfate and magnesium sulfate) and freed of solvent in vacuo. The remaining material was chromatographed on silica gel (50 g) eluting with ether:hexane (1:3) followed by (1:1) to give the title compound (643.1 mg, 71%). TLC:$R_f$=0.21, silica gel, ether:hexane (1:3), cobalt stain.

B.
4'-[[(2-Ethoxy-1-methyl-2-oxoethyl)amino]methyl][1,1'-biphenyl]-2-carboxylic acid, 1,1-dimethylethyl ester The title A compound (310.7 mg, 1.10 mmol, 1.0 eq), sodium acetate (90.2 mg, 1.10 mmol, 1.0 eq) and DL-alanine ethyl ester hydrochloride (169 mg, 1.10 mmol, 1.0 eq) were dissolved in methanol (11 mL, 0.1 M) in an argon atmosphere. The solution was cooled in an ice bath and sodium cyanoborohydride (69 mg, 1.10 mmol, 1 eq) was added (pH 5–6). The mixture was stirred at room temperature two hours, then quenched by adding 1 N hydrochloric acid to pH 1. The quenched reaction mixture was stirred at room temperature for one hour. A small amount of water was then added followed by solid sodium bicarbonate to render the mixture neutral. The product was extracted into chloroform (3×30 mL). The combined extracts were washed once with saturated sodium bicarbonate solution, dried (magnesium sulfate) and freed of solvent in vacuo. The remaining material was purified by chromatography on silica gel (40 g) eluting with ether:hexane (1:2) to give the title compound (242 mg, 57%). TLC:$R_f$=0.26, silica gel, ether: hexane(1:1), UV.

C. [(Propylamino)thioxomethyl]]carbamic acid, 1,1-dimethylethyl ester

The title A compound of Example 1 (500 mg, 4.23 mmol, 1.0 eq) was dissolved in distilled tetrahydrofuran (42 mL, 0.1 M) and the solution was cooled to 0° C. Sodium hydride (508 mg of 50% in mineral oil, 10.8 mmol, 2.5 eq) was added and the mixture was stirred cold 20 minutes. Di-, tert-butyl dicarbonate (1.20 g, 5.5 mmol, 1.3 eq) was added. The mixture was stirred cold 15 minutes, then at room temperature one hour. The reaction was quenched by adding ammonium chloride solution and adjusting to pH 5 with 1 N hydrochloric acid solution. The product was extracted into chloroform, dried (magnesium sulfate) and freed of solvent in vacuo to give the title compound (892 mg, 96%) as a yellow oil.

TLC:$R_f$=0.52, silica gel, ether:hexane (1:3), UV and Cerium.

D.
4'-[[3-[1,1-(Dimethylethoxy)carbonyl]tetrahydro-5-methyl-4-oxo-2-(propylimino)-1H-imidazol-1-yl]methyl][1,1'-biphenyl]-2-carboxylic acid, 1,1-dimethylethyl ester.

The title B compound (191.7 mg, 0.50 mmol, 1.0 eq) was dissolved in dimethylformamide (1.0 mL, 0.5 M) in an argon atmosphere. The title C compound (132 mg, 0.61 mmol, 1.2 eq), ethyl-3-(3-dimethylamino) propyl carbodiimide, hydrochloride (116 mg, 0.61 mmol, 1.2 eq) and triethylamine (85 μl, 0.61 mmol, 1.2 eq) were added and the mixture was left stirring overnight at room temperature. Water (20 mL) was added and the mixture was extracted three times with ethyl acetate.

The extracts were dried (magnesium sulfate) and the solvent was removed in vacuo. The product was purified by chromatography on silica gel (40 g) eluting with ether:hexane (1:2) to give the title compound (215 mg, 85%).

TLC: $R_f$=0.31, silica gel, 20% acetone in hexane, UV.

E. 4'-[[4,5-Dihydro-5-methyl-4-oxo-2-(propylamino)-1H-imidazol-1-yl]-methyl]-[1,1'-biphenyl-2-carboxylic acid, trifluoroacetate (1:1) salt The title D compound (215 mg, 0.412 mmol, 1.0 eq) was treated with 8 mL of 4 N hydrochloric acid in dioxane. The mixture was stirred at room temperature 7 hours. The solvent was removed in vacuo. The product was purified by preparative HPLC on a YMC S-10 ODS, 30×500 mm column, using a flow rate of 25 mL/min of 59.6% methanol in water containing 0.7% triflouroroacetic acid and detecting at 230 mµ. The material collected at 15¾ to 18¾ minutes was concentrated to a small volume and lyophilized. The product was redissolved in water, passed through a polycarbonate filter and relyophilized to give the title compound (168 mg, 82%).

What is claimed is:

1. A compound of the formula

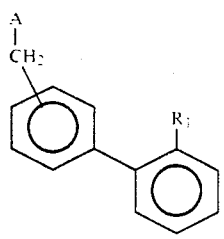

where A is

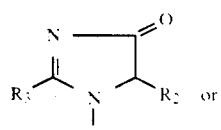

pharmaceutically acceptable salts thereof; where $R_1$ is hydrogen, —COOH, —NHSO$_2$CF$_3$,

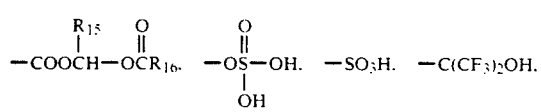

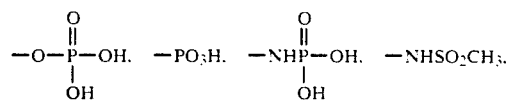

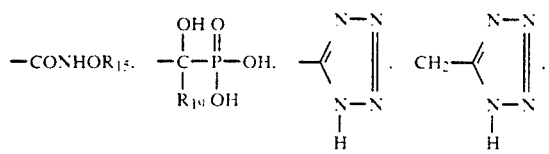

-continued

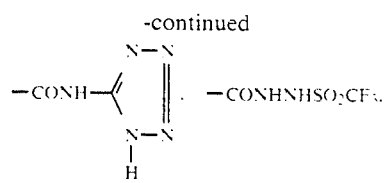

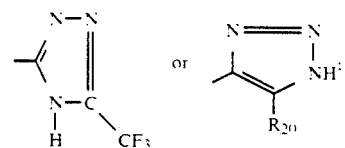

$R_2$ is H, alkyl of 1 to 10 carbon atoms, alkenyl of 3 to 10 carbon atoms, or the same groups substituted with F; phenylalkenyl wherein the aliphatic portion is 2 to 6 carbon atoms; —(CH$_2$)$_m$-imidazol-1-yl; —(CH$_2$)$_m$-1,2,3-triazolyl optionally substituted with one or two groups selected from CO$_2$R$_7$ or alkyl of 1 to 4 carbon atoms; —(CH$_2$)$_m$-tetrazolyl; —(CH$_2$)$_n$OR$_6$;

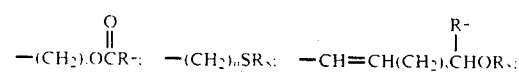

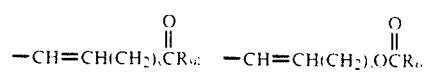

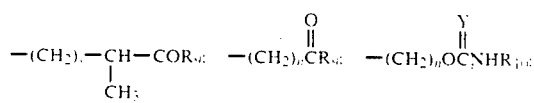

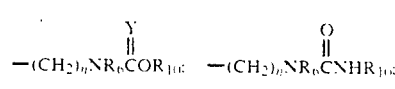

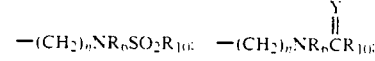

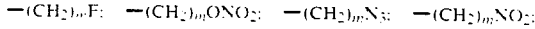

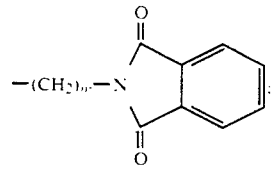

$R_3$ is alkyl of 2 to 10 carbon atoms, alkenyl or alkynyl of 3 to 10 carbon atoms or the same groups substituted with F or CO$_2$R$_7$; cycloalkyl of 3 to 8 carbon atoms, cycloalkylalkyl of 4 to 10 carbon atoms; cycloalkylalkenyl or cycloalkylalkynyl of 5 to 10 carbon atoms; —(CH$_2$)$_s$Z(CH$_2$)$_m$R' (wherein R' is H, C$_{1-6}$alkyl, C$_{3-6}$cycloalkyl, C$_{2-4}$alkenyl or C$_{2-4}$alkynyl) optionally substituted with F or CO$_2$R$_7$; benzyl or benzyl substituted on the phenyl ring with 1 or 2 halogens, alkoxy of 1 to 4 carbon atoms, alkyl of 1 to 4 carbon atoms or nitro;

$R_6$ is H, alkyl of 1 to 6 carbon atoms, cycloalkyl of 3 to 6 carbon atoms, phenyl or benzyl;

$R_7$ to H, alkyl or perfluoroalkyl of 1 to 8 carbon atoms, cycloalkyl of 3 to 6 carbon atoms, phenyl or benzyl;

$R_8$ is H, alkyl of 1 to 6 carbon atoms, cycloalkyl of 3 to 6 carbon atoms, phenyl, benzyl, acyl of 1 to 4 carbon atoms, phenacyl;
$R_9$ is H, alkyl of 1 to 6 carbon atoms, cycloalkyl of 3 to 6 carbon atoms, $(CH_2)_pC_6H_5$, $OR_{11}$ or $NR_{12}R_{13}$;
$R_{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;
$R_{11}$ is H, alkyl of 1 to 6 carbon atoms, cyclalkyl of 3 to 6 carbon atoms, phenyl or benzyl;
$R_{12}$ and $R_{13}$ independently are H, alkyl of 1 to 4 carbon atoms, phenyl, benzyl, α-methylbenzyl, or taken together form a ring of the formula

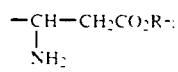

Q is $NR_{14}$, O or $CH_2$;
$R_{14}$ and $R_{15}$ are independently H, alkyl, aryl, aralkyl or cycloalkyl;
$R_{16}$ is $C_{1-6}$alkyl, $-NR_{17}R_{18}$ or

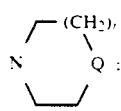

$R_{17}$ and $R_{18}$ are independently H, $C_{1-6}$alkyl, benzyl or taken together are 3 to 6 carbon atoms forming a 4- to 7-membered ring with the nitrogen atom to which they are attached;
$R_{19}$ is H, $C_{1-5}$alkyl, phenyl;
$R_{20}$ is $-CN$, $-NO_2$ or $-CO_2R_7$;
Y = O or S;
Z = O, $NR_6$ or S;
m is 1-5;
n is 1-10;
p is 0-3;
s is 0-5; and
t is 0 or 1.

2. The compound of formula I as recited in claim 1 wherein
$R_1$ is independently COOH or tetrazole;
$R_2$ is selected from methyl, ethyl, $-CH_2OH$; and
$R_3$ is selected from n-butyl, n-propyl, NH-n-propyl.

3. The compound of formula I as recited in claim 1 wherein A is

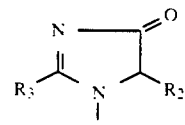

and
$R_1$ is COOH;
$R_2$ is methyl; and
$R_3$ is propylamino.

4. The compound of formula I as recited in claim 1 having the name 4'-[[4,5-Dihydro-5-methyl-4-oxo-2-(propylamino)-1H-imidazol-1-yl]methyl]-[1,1'-biphenyl]-2-carboxylic acid, trifluoroacetate (1:1) salt.

5. A pharmaceutical composition comprising a compound of formula I as recited in claim 1 and a pharmaceutically acceptable carrier.

6. A method of treating hypertension comprising administering to a mammalian specie in need thereof a therapeutically effective amount of a composition of claim 5.

7. A method for treating congestive heart failure comprising administering to a mammalian specie in need thereof a therapeutically effective amount of a composition of claim 5.

8. A method for preventing cardiac hypertrophy comprising administering to a mammalian specie in need thereof a therapeutically effective amount of a composition of claim 5.

* * * * *